United States Patent
Boissard et al.

(10) Patent No.: US 10,888,720 B2
(45) Date of Patent: Jan. 12, 2021

(54) GENTIOPICROSIDE FREE GENTIANA EXTRACT

(71) Applicant: DSM IP ASSETS B.V., Heerlen (NL)

(72) Inventors: Christophe Boissard, Kaiseraugst (CH); Dominik Imfeld, Kaiseraugst (CH); Marie-Sophie Meisinger, Kaiseraugst (CH); François Paul, Kaiseraugst (CH)

(73) Assignee: DSM IP ASSETS B.V., Heerlen (NL)

( * ) Notice: Subject to any disclaimer, the term of this patent is extended or adjusted under 35 U.S.C. 154(b) by 112 days.

(21) Appl. No.: 15/575,955

(22) PCT Filed: Jun. 2, 2016

(86) PCT No.: PCT/EP2016/062541
§ 371 (c)(1),
(2) Date: Nov. 21, 2017

(87) PCT Pub. No.: WO2016/193390
PCT Pub. Date: Dec. 8, 2016

(65) Prior Publication Data
US 2018/0147136 A1    May 31, 2018

Related U.S. Application Data

(60) Provisional application No. 62/170,986, filed on Jun. 4, 2015.

(30) Foreign Application Priority Data

Aug. 21, 2015    (EP) .................................... 15181916

(51) Int. Cl.
| | | |
|---|---|---|
| A61K 36/51 | (2006.01) | |
| A61K 36/00 | (2006.01) | |
| A61Q 19/08 | (2006.01) | |
| A61K 8/9789 | (2017.01) | |
| A61P 17/18 | (2006.01) | |
| A61P 17/00 | (2006.01) | |
| A61K 8/06 | (2006.01) | |
| A61K 36/515 | (2006.01) | |
| A61Q 19/04 | (2006.01) | |
| C12P 17/18 | (2006.01) | |

(52) U.S. Cl.
CPC .............. *A61Q 19/08* (2013.01); *A61K 8/062* (2013.01); *A61K 8/9789* (2017.08); *A61K 36/515* (2013.01); *A61P 17/00* (2018.01); *A61P 17/18* (2018.01); *A61Q 19/04* (2013.01); *C12P 17/181* (2013.01); *C12Y 302/01021* (2013.01); *A61K 2236/333* (2013.01); *A61K 2236/53* (2013.01); *A61K 2236/55* (2013.01); *A61K 2800/30* (2013.01); *A61K 2800/522* (2013.01); *A61K 2800/78* (2013.01); *A61K 2800/782* (2013.01)

(58) Field of Classification Search
None
See application file for complete search history.

(56) References Cited

FOREIGN PATENT DOCUMENTS

| | | |
|---|---|---|
| CN | 1437953 | 8/2003 |
| CN | 102488745 | 6/2012 |
| CN | 102631311 | 8/2012 |
| DE | 019834813 A1 * | 2/2000 |
| FR | 2 926 991 | 8/2009 |
| FR | 2 990 350 | 11/2013 |
| WO | WO 02/055047 | 7/2002 |

OTHER PUBLICATIONS

Guangqun (Plant composition extracting solution as well as extraction method and application thereof, CN104367502A, pp. 1-14, Publication Feb. 25, 2015) (Year: 2015).*
International Search Report for PCT/EP2016/062541 dated Oct. 14, 2016, 4 pages.
K. Ishiguro et al., "Studies on Indroid-related Compounds III: Gentiopicral, the Aglucone of Gentiopicroside", Planta Medica, vol. 49, No. 12, Dec. 1, 1983, pp. 208-210.
Öztürk: "Effects of Gentiopicroside, Sweroside and Swertiamarine, Secoiridoids from Gentian (*Gentiana lites* ssp. *Symphyandra*), on cultured chicken embryonic fibroblasts", Planta Med 2006, vol. 72, Feb. 10, 2005, pp. 289-294.

* cited by examiner

*Primary Examiner* — Michael Barker
(74) *Attorney, Agent, or Firm* — Nixon & Vanderhye P.C.

(57) ABSTRACT

The present invention relates to gentiopicroside free *Gentiana acaulis* and/or *Gentiana septemfida* extracts. Furthermore, it relates to cosmetic compositions comprising such gentiopicroside free *Gentiana acaulis* or *Gentiana septemfida* extract, as well as mixtures thereof.

9 Claims, No Drawings

GENTIOPICROSIDE FREE GENTIANA EXTRACT

This application is the U.S. national phase of International Application No. PCT/EP2016/062541 filed Jun. 2, 2016 which designated the U.S. and claims priority to U.S. Provisional Application No. 62/170,986 filed Jun. 4, 2015 and EP Patent Application No. 15181916.6 filed Aug. 21, 2015, the entire contents of each of which are hereby incorporated by reference.

The present invention relates to gentiopicroside free *Gentiana acaulis* and/or *Gentiana septemfida* extracts. Furthermore, it relates to cosmetic compositions comprising such gentiopicroside free *Gentiana acaulis* or *Gentiana septemfida* extract, as well as mixtures thereof.

It is increasingly important for humans to look healthy, and a beautiful skin with limited wrinkles is always perceived as a sign of good health. There are many cosmetic ingredients claiming cosmetic effects, but some of them are either difficult to formulate, poorly soluble in cosmetic preparations, unstable during storage of the final cosmetic product, or present signs of toxicity or even generate allergic reactions when used on a regular basis.

In the aging process, various signs appear on the skin resulting from a modification of skin structure and of cutaneous function.

A signature sign of aging skin, regardless of the etiology, is loss of elasticity resulting from reduced production of collagen and the degradation of existing collagen. Collagens are fibrous structural proteins and a main component of the extracellular matrix of connective tissue. Collagen contributes to the strength and elasticity of human skin, and its degradation leads to changes in the appearance and/or function of the skin, such as wrinkles, including fine, superficial wrinkles and coarse, deep wrinkles, lines, crevices, bumps, enlarged pores, scariness, flakiness loss of skin elasticity, sagging (including puffiness in the eye area and jowls), loss of skin firmness, compromised barrier properties, discoloration (including under-eye circles), blotching, sallowness, mottled pigmentation, age spots, freckles, keratoses, abnormal differentiation, hyper-keratinization, elastosis, telangiectasia and other histological changes in the stratum corneum, dermis, epidermis, the skin vascular system. Moreover, there is a continuing trend in the art to provide naturally-derived skin care ingredients for application to the skin.

Thus, there is an ongoing need for natural ingredients and natural plant extracts having cosmetic benefits, particularly regarding skin aging, being easy to formulate, and safe for the end user.

*Gentiana* extracts such as e.g. *Gentiana acaulis* extracts have been disclosed in the prior art to have beneficial effects on skin (FR2990350). These *gentiana* extracts, however, contain significant amounts of gentiopicroside (CAS No. 20831-76-9), a secoiridoid glucoside which has been reported to have DNA damaging, mutagenic, and clastogenic effects (K. Mustafayeva et al. /J. Nat. Prod. 2010, 73, 99-103). Due to safety concerns, *Gentiana* extracts therefore are not yet found in commercial cosmetic products and there is an ongoing need for a Genitiana extract which are free of gentiopicroside while still providing beneficial cosmetic effects.

The present inventors now have found a way to provide gentiopicroside free *gentiana* extracts which still exhibit excellent cosmetic benefits.

Thus, in a first embodiment the present invention relates to a *Gentiana acaulis* and/or a *Gentiana septemfida* extract which is substantially free of gentiopicroside.

In another embodiment the present invention relates to a process for the preparation of a *Gentiana acaulis* and/or *Gentiana septemfida* extract which is substantially free of gentiopicroside, said process comprising the steps of
(i) Extracting the aerial parts (flower, leaf, stem) of *Gentiana acaulis* and/or *Gentiana septemfida* with a water/organic solvent mixture to obtain, after filtration of the aerial parts, an extract comprising gentiopicroside, followed by
(ii) Removal of the organic solvent to obtain an aqueous extract, followed by
(iii) Hydrolysis of the gentiopicroside in the aqueous extract to gentiopicral.

*Gentiana acaulis* (stemless gentian) is a species of flowering plant in the family Gentianaceae, native to central and southern Europe, from Spain east to the Balkans, growing especially in mountainous regions, such as the Alps, Cevennes and Pyrenees, at heights of 800-3,000 meters.

It is a perennial plant, growing to 2 cm tall and 10 cm or more wide. The leaves are evergreen, 2-3.5 cm long, in a basal rosette, forming clumps. The trumpet-shaped terminal flowers are blue with olive-green spotted longitudinal throats. They grow on a very short peduncle, 3-6 cm long. The flower stem is often without leaves, or has 1 or 2 pairs of leaves. It likes full sun, is fully hardy and flowers in late spring and summer. This plant, like others of its genus, is valued in cultivation for the unusually pure intense blue of its blooms.

*Gentiana septemfida* (crested gentian or summer gentian) is a species of flowering plant in the family Gentianaceae, native to the Caucasus and Turkey. It is a low-growing herbaceous perennial growing to 15-20 cm tall by 30 cm wide, bearing up to eight bright blue trumpet-shaped blooms in summer, with striped interiors. It requires a rich, moist soil and full sun.

The term 'substantially free of' as used herein refers to concentrations of less than 0.5%. Preferably the concentration of gentiopicroside is less than 0.1%, more preferably less than 0.0 1%, most preferably less than 0.001%. In particular, the extract contains no detectable gentiopicroside anymore (all % given for the concentration of gentiopicroside in the extract are area-% measured by UPLC (column: C-18 reversed phase column, eluent: water/acetonitrile) and UV detection @ 254 nm).

In all embodiments of the present invention, the extracts are preferably also substantially free of gentiopicral which is removed from the aqueous extract obtained in (iii) in a subsequent extraction step (iv).

In all embodiments according to the present invention, the gentiopicral concentration in the *Gentiana acaulis* and/or *Gentiana septemfida* extract according to the present invention is preferably less than 1%. More preferably the concentration of gentiopicral is less than 0.5%, most preferably less than 0.1%, such as in particular less than 0.01%. the extraction is performed until the extract contains no detectable gentiopicral anymore. (all % given for the concentration of gentiopicral in the extract are area-% measured by UPLC (column: C-18 reversed phase column, eluent: water/acetonitrile) and UV detection @ 254 nm).

Preferably the organic solvent used for the extraction of the aerial parts is selected from the group consisting of $C_1$-$C_6$ alcohols, more preferably from methanol, ethanol and isopropanol as well as mixtures thereof. Most preferably, the organic solvent is ethanol.

In all embodiments of the present invention the amount of water in the water/organic solvent mixture is preferably selected in the range of 10-50 wt.-%, more preferably in the range of 30-50 wt.-%, such as most preferably in the range of 35 to 45 wt.-% wt.-% based on the total weight of the solvent mixture.

The amount of water/organic solvent mixture used for the extraction of the aerial parts is preferably selected in the range of 1 to 50 wt.-%, preferably in the range 5 to 30 wt.-%, most preferably in the range of 5 to 15 wt.-% such as in the range of 10 to 12 wt.-% based on the weight of the aerial parts.

In a preferred embodiment, the water/organic solvent mixture contains an effective amount of active charcoal, preferably in an amount of 5-20% (w/w) based on the dried plant parts used, more preferably in an amount of 10-25% (w/w).

In a preferred embodiment, the aerial parts are chopped before extraction.

In the case of the use of *Gentiana acaulis* and *Gentiana septemfida* (to obtain a *Gentiana acaulis* and *Gentiana septemfida* extract), the dried plant parts are mixed prior to extraction. Alternatively, the respective extracts can be prepared individually and mixed after preparation to obtain the extract consisting of *Gentiana acaulis* and *Gentiana septemfida*.

The extraction of the aerial parts is preferably performed at a temperature selected in the range of 30-60° C., preferably in the range 45-55° C., most preferably at about 50° C. for a period of 1 to 5 h, preferably of 1.5 to 3 h. Most preferred, the extraction is carried out for 2 h at 50° C.

The hydrolysis of gentiopicroside to gentiopicral in the aqueous extract is preferably done using a β-glucosidase (EC 3.2.1.21), more preferably a β-glucosidase bound to a solid phase such as to an epoxy-activated resin, in particular an epoxy-activated methacrylic/styrene resin. Such resins are e.g. commercially available under the tradename Purolite. The hydrolysis is preferably performed until the concentration of gentiopicroside is within the limits as outlined above, preferably however until no gentiopicroside is detectable anymore by UPLC.

The extraction of gentiopicral is preferably performed using an organic solvent. Suitable organic solvents for the extraction of gentiopicral can easily be selected by a person skilled in the art and encompass ethers such as diethylether or tert.-butylether, ketones such as acetone, ester solvents such as ethyl acetate, halogenated solvents such as chloroform and dichloromethane as well as aromatic hydrocarbon solvents such as toluene and benzene. A particular suitable solvent for the removal of gentiopicral is however ethyl acetate as it has the advantage to selectively remove gentiopicral without removal of the other active ingredients (in particular flavonoids) necessary for achieving the desired cosmetic effects.

Removal (evaporation) of the solvents can be performed by standard methods in the art, e.g. by evaporation in a Rotavap device at 50° C. and 50 mbar atmosphere.

In a preferred embodiment, the processes according to the present invention further contain a step (ii-1) following step (ii), which step consists in treating a concentrated aqueous extract obtained in (ii) with pure ethanol (i.e. ETOH abs.) to precipitate any sugars and/or proteins followed by filtration and evaporation of the ethanol. Preferably, the precipitation takes place for 1 h to 36 h, more preferably for 12 h-30 h, most preferably for 18-28 h. The amount of ethanol in this step is preferably about 2 to 8 times the amount of the aqueous extract, preferably about 4 to 6 times. The amount of ethanol used for the precipitation is preferably at least 2 times the amount of the aqueous extract, more preferably the amount is selected 4 to 6 times the amount of the aqueous extract.

In a preferred embodiment, the gentiopicroside free *Gentiana acaulis* and/or *Gentiana septemfida* extract(s) according to the present invention are standardized on Flavonoid content calculated as isorientin. Main active chemical compounds in the extract consist in: iridoids and seco-iridoids: swertiamarine, sweroside, gelidoside, trifloroside, and flavonoids: iso-orientin, iso-vitexin, isoorientin-4'-O-Glucoside, and iso-saponarin.

In a particular advantageous embodiment, the flavonoid content in the extract according to the present invention is in the range of 1 to 6 wt.-%, preferably in the range of 2 to 5 wt.-%, based on the dry extract.

The gentiopicroside free *Gentiana acaulis* and/or *Gentiana septemfida* extract(s) according to the present invention can be used as aqueous extract or in dried (powder) form.

In a particular preferred embodiment, the gentiopicroside free *Gentiana* extract according to the present invention is an extract of a mixture of the aerial parts of *Gentiana acaulis* and *Gentiana septemfida*. More preferably, the mixture consists in a ratio of *Gentiana acaulis* to *Gentiana septemfida* comprised between 5/95 mass/mass and 50/50 mass/mass, even more preferably, the ratio of *Gentiana acaulis* to *Gentiana septemfida* is comprised between 10/90 mass/mass and 30/70 mass/mass, most preferably, the ratio of aerial parts of *Gentiana acaulis* to *Gentiana septemfida* is comprised between 15/85 mass/mass and 25/75 mass/mass.

Surprisingly it has been found that the use of the gentiopicroside free *Gentiana acaulis* extract and/or *Gentiana septemfida* extract according to the present invention still exhibits the beneficial cosmetic effects, more particularly regarding anti-aging effects.

Thus, the invention also relates to cosmetic compositions comprising such gentiopicroside free *Gentiana acaulis* and/or *Gentiana septemfida* extract(s). Furthermore it relates to the cosmetic use of a composition comprising such gentiopicroside free *Gentiana acaulis* and/or *Gentiana septemfida* extract(s). It also relates to a method of cosmetic treatment, said method comprising topically applying onto the skin of an individual seeking such treatment a cosmetic composition comprising such gentiopicroside free *Gentiana acaulis* and/or *Gentiana septemfida* extract(s).

The term "cosmetic composition" as used herein refers to any substance or preparation intended to be placed in contact with any part of the external surfaces of the human body (that is to say, the epidermis, hair system, nails, lips and external genital organs), or with the teeth and the mucous membranes of the oral cavity, with a view exclusively or mainly to cleaning them, perfuming them, changing their appearance, protecting them, keeping them in good condition or correcting body odours, except where such cleaning, perfuming, protecting, changing, keeping, or correcting is wholly for the purpose of treating or preventing disease'.

Preferably, in all embodiments of the present invention, the cosmetic composition according to the present invention comprises between 0.001 and 20 wt-% of a gentiopicroside free *Gentiana acaulis* extract, a gentiopicroside free *Gentiana septemfida* extract, or mixture thereof (based on the dry matter). More preferably, the cosmetic composition comprises between 0.01 and 10 wt-%, even more preferably, it comprises between 0.01 and 5 weight-%, of a *Gentiana acaulis* extract, *Gentiana septemfida* extract, or mixture thereof.

According to the present invention, the *Gentiana acaulis* extract, *Gentiana septemfida* extract, or mixtures thereof can be used as such or in an encapsulated form, for example in a liposomal form. Liposomes are preferably formed with lecithins with or without addition of sterols or phytosterols. The encapsulation of the active ingredients can be alone or together with other active ingredients. Other embodiments include solid or semisolid capsules aiming to protect the *Gentiana acaulis* extract, *Gentiana septemfida* extract, or mixture thereof from degradation or for controlled delivery. Suitable encapsulation technologies are for example described in WO 0180823, WO 9903450, WO 9317784 or in Fragrance Journal (2001), 29(2), 83-90.

Preferred cosmetic composition according to the present invention is a topical composition, more preferably it further comprises a conventional cosmetic carrier, even more preferably, it is a skin (face and body) care preparation, a decorative preparation, a light protection preparation, or a functional preparation.

Examples of skin care preparations are, in particular, face creams, body oils, body lotions, body gels, treatment creams, skin protection ointments, shaving preparations, such as shaving foams or gels, moisturizing gels, moisturizing sprays, revitalizing body sprays, cellulite gels, face and/or body moisturizers, facial and/or body cleansers, and face masks. Most preferred are face care products.

Preferred topical cosmetic compositions according to the invention are skin care preparations, or functional preparations.

Examples of decorative preparations are, in particular, lipsticks, eye shadows, mascaras, dry and moist make-up formulations, rouges, powders, and/or suntan lotions.

Examples of functional preparations are cosmetic compositions containing further active ingredients such as hormones, vitamins, vegetable and/or fruit extracts, anti-ageing ingredients, and/or antimicrobial (antibacterial or antifungal) ingredients without being limited thereto.

Cosmetic composition for use in accordance with the invention can be in the form of a liquid, lotion, a thickened lotion, a gel, a cream, a milk, an ointment, a paste, a powder, a make-up, or a solid tube stick and can be optionally be packaged as an aerosol and can be provided in the form of a mousse such as a aerosol mousse, a foam or a spray foams, sprays, sticks, a gel, a plaster, a powder, a cleanser, a soap or aerosols or wipes. Preferred topical compositions comprise a cream, an emulsion, a gel, an ointment, a lotion a tincture, a spray, a mousse, a cleansing composition or foam.

In another embodiment, the cosmetic composition for use according to the present invention is characterized in that it further comprises at least one UV screening agent, and/or a moisturizer, and/or an anti-aging agent, and/or a skin tone agent, and a conventional cosmetic carrier.

Conventional cosmetic carriers comprise excipients or diluents conventionally used in topical compositions. The necessary amounts of the cosmetic and dermatological adjuvants and additives can, based on the desired product, easily be determined by the skilled person.

Regarding the kind of the topical cosmetic composition and the preparation of the topical cosmetic preparations as well as for further suitable additives, it can be referred to the pertinent literature, e.g. to Novak G. A., Die kosmetischen Präparate—Band 2, Die kosmetischen Präparate—Rezeptur, Rohstoffe, wissenschaftliche Grundlagen (Verlag für Chem. Industrie H. Ziolkowski K G, Augsburg).

Preferably, the topical cosmetic compositions used in the present invention are in the form of a suspension or dispersion in solvents or fatty substances, or alternatively in the form of an emulsion or micro emulsion (in particular of O/W or W/O type, O/W/O or W/O/W-type), PET-emulsions, multiple emulsions, bickering emulsions, hydrogels, alcoholic gels, lipogels, one or multiphase solutions or a vesicular dispersion and other usual compositions, which can also be applied by pens, as masks or as sprays. The emulsions can also contain anionic, nonionic, cationic or amphoteric surfactant(s).

The topical cosmetic compositions used in the present invention can also contain usual cosmetic adjuvants and additives, such as preservatives/antioxidants, fatty substances/oils, water, organic solvents, silicones, thickeners, softeners, emulsifiers, sunscreens, antifoaming agents, moisturizers, fragrances, surfactants, fillers, sequestering agents, anionic, cationic, nonionic or amphoteric polymers or mixtures thereof, propellants, acidifying or basifying agents, dyes, colorants, pigments or nanopigments, e.g. those suited for providing a photoprotective effect by physically blocking out ultraviolet radiation, or any other ingredients usually formulated into topical cosmetic compositions. The necessary amounts of the cosmetic and dermatological adjuvants and additives can, based on the desired product, easily be chosen by a skilled artisan in this field and will be illustrated in the examples, without being limited hereto. The usual cosmetic adjuvants and additives such as emulsifiers, thickeners, surface active ingredients and film formers can show synergistic which can be determined by the expert in the field with normal trials, or with the usual considerations regarding the formulation of topical cosmetic composition.

Typically topical cosmetic compositions also contain surface active ingredients like emulsifiers, solubilizers and the like. An emulsifier enables two or more immiscible components to be combined homogeneously. Moreover, the emulsifier acts to stabilize the composition. Solubilizers that may be used in the present invention include but are not restricted to PEG/PPG-18/18 Dimethicone, PEG-40 Hydrogenated Castor Oil, PEG-20 Stearate, PEG-30 Glyceryl Stearate, and PEG-7 Glyceryl Cocoate. Emulsifiers that may be used in the present invention in order to form OW, W/O, O/W/O or W/O/W emulsions/microemulsions include sorbitan oleate, sorbitan sesquioleate, sorbitan isostearate, sorbitan trioleate, polyglyceryl-3-diisostearate, polyglycerol esters of oleic/ isostearic acid, polyglyceryl-6 hexaricinolate, polyglyceryl-4-oleate, polyglyceryl-4-oleate/PEG-8 propylene glycol cocoate, oleamide DEA, TEA myristate, TEA stearate, magnesium stearate, sodium stearate, potassium laurate, potassium ricinoleate, sodium cocoate, sodium tallowate, potassium castorate, sodium oleate, and mixtures thereof. Furthermore, one or more synthetic polymers may be used as an emulsifier. For example, PVP eicosene copolymer, acrylates/$C_{10-30}$ alkyl acrylate crosspolymer, acrylates/ steareth-20 methacrylate copolymer, PEG-22/dodecyl glycol copolymer, PEG-45/dodecyl glycol copolymer, and mixtures thereof. The preferred emulsifiers are PVP Eicosene copolymer, acrylates/$C_{10-30}$-alkyl acrylate crosspolymer, PEG-20 sorbitan isostearate, sorbitan isostearate, and mixtures thereof. The one or more emulsifiers are present in a total amount about 0.01 wt. % to about 20 wt. % of the total weight of the topical cosmetic composition for use in the present invention. Preferably, about 0.1 wt. % to about 10 wt. % of emulsifiers is used.

The lipid phase of the topical cosmetic compositions can advantageously be chosen from: mineral oils and mineral waxes; oils such as triglycerides of caprinic acid or caprylic acid and castor oil; oils or waxes and other natural or synthetic oils, in a preferred embodiment esters of fatty acids with alcohols e.g. isopropanol, propylene glycol, glycerin or esters of fatty alcohols with carboxylic acids or fatty acids; alkylbenzoates; and/or silicone oils such as dimethylpolysiloxane, diethylpolysiloxane, diphenylpolysiloxane, cyclomethicones and mixtures thereof.

Exemplary fatty substances which can be incorporated in the oil phase of the emulsion, microemulsion, oleo gel, hydrodispersion or lipodispersion of the topical cosmetic composition of the present invention are advantageously chosen from esters of saturated and/or unsaturated, linear or branched alkyl carboxylic acids with 3 to 30 carbon atoms, and saturated and/or unsaturated, linear and/or branched alcohols with 3 to 30 carbon atoms as well as esters of aromatic carboxylic acids and of saturated and/or unsaturated, linear or branched alcohols of 3-30 carbon atoms. Such esters can advantageously be selected from octylpalmitate, octylcocoate, octylisostearate, octyldodecylmyristate, cetearylisononanoate, isopropylmyristate, isopropylpalmitate, isopropylstearate, isopropyloleate, n-butylstearate, n-hexyllaureate, n-decyloleate, isooctylstearate, isononylstearate, isononylisononanoate, 2-ethyl hexylpalmitate, 2-ethylhexyllaurate, 2-hexyldecylstearate, 2-octyldodecylpalmitate, stearylheptanoate, oleyloleate, oleylerucate, erucyloleate, erucylerucate, tridecylstearate, tridecyl-trimellitate, as well as synthetic, half-synthetic or natural mixtures of such esters e.g. jojoba oil.

Other fatty components suitable for use in the topical cosmetic compositions for use according to the present invention include polar oils such as lecithins and fatty acid triglycerides, namely triglycerol esters of saturated and/or unsaturated, straight or branched carboxylic acid with 8 to 24 carbon atoms, preferably of 12 to 18 carbon-atoms whereas the fatty acid triglycerides are preferably chosen from synthetic, half synthetic or natural oils (e.g. cocoglyceride, olive oil, sun flower oil, soybean oil, peanut oil, rape seed oil, sweet almond oil, palm oil, coconut oil, castor oil, hydrogenated castor oil, wheat oil, grape seed oil, macadamia nut oil and others); apolar oils such as linear and/or branched hydrocarbons and waxes e.g. mineral oils, vaseline (petrolatum); paraffins, squalane and squalene, polyolefins, hydrogenated polyisobutenes and isohexadecanes, favored polyolefins are polydecenes; dialkyl ethers such as dicaprylylether; linear or cyclic silicone oils such as preferably cyclomethicones (octamethylcyclotetrasiloxane; cetyldimethicone, hexamethylcyclotrisiloxane, polydimethylsiloxane, poly(methylphenylsiloxane) and mixtures thereof.

Other fatty components which can advantageously be incorporated in topical cosmetic compositions for use according to the present invention are isoeikosane; neopentylglycoldiheptanoate; propyleneglycoldicaprylate/dicaprate; caprylic/capric/diglycerylsuccinate; butyleneglycol caprylat/caprat; $C_{12-13}$-alkyllactate; di-$C_{12-13}$ alkyltartrate; triisostearin; dipentaerythrityl hexacaprylat/hexacaprate; propylene-glycolmonoisostearate; tricaprylin; dimethylisosorbid. Especially beneficial is the use of mixtures $C_{12-15}$-alkylbenzoate and 2-ethylhexylisostearate, mixtures $C_{12-15}$-alkylbenzoate and isotridecylisononanoate as well as mixtures of $C_{12-15}$-alkylbenzoate, 2-ethylhexylisostearate and isotridecylisononanoate.

The oily phase of the topical cosmetic compositions for use according to the present invention can also contain natural vegetable or animal waxes such as bee wax, china wax, bumblebee wax and other waxes of insects as well as Shea butter and cocoa butter.

A moisturizing agent may be incorporated into a topical cosmetic composition used according to the present invention to maintain hydration or rehydrate the skin. Moisturizers that prevent water from evaporating from the skin by providing a protective coating are called emollients. Additionally an emollient provides a softening or soothing effect on the skin surface and is generally considered safe for topical use. Preferred emollients include mineral oils, lanolin, petrolatum, capric/caprylic triglyceraldehydes, cholesterol, silicones such as dimeticone, cyclometicone, almond oil, jojoba oil, avocado oil, castor oil, sesame oil, sunflower oil, coconut oil and grape seed oil, cocoa butter, olive oil aloe extracts, fatty acids such as oleic and stearic, fatty alcohols such as cetyl and hexadecyl (ENJAY), diisopropyl adipate, hydroxybenzoate esters, benzoic acid esters of $C_{9-15}$-alcohols, isononyl iso-nonanoate, ethers such as polyoxypropylene butyl ethers and polyoxypropylene cetyl ethers, and $C_{12-15}$-alkyl benzoates, and mixtures thereof. The most preferred emollients are hydroxybenzoate esters, aloe vera, $C_{12-15}$-alkyl benzoates, and mixtures thereof. An emollient is present in an amount of about 1 wt. % to about 20 wt. % of the total weight of the topical cosmetic composition. The preferred amount of emollient is about 2 wt. % to about 15 wt. %, and most preferably about 4 wt. % to about 10 wt. %.

Moisturizers that bind water, thereby retaining it on the skin surface are called humectants. Suitable humectants can be incorporated into a topical cosmetic composition of the present invention such as glycerin, polypropylene glycol, polyethylene glycol, lactic acid, pyrrolidone carboxylic acid, urea, phospholipids, collagen, elastin, ceramides, lecithin sorbitol, PEG-4, and mixtures thereof. Additional suitable moisturizers are polymeric moisturizers of the family of water soluble and/or swellable/and/or with water gelating polysaccharides such as hyaluronic acid, chitosan and/or a fucose rich polysaccharide which is e.g. available as Fucogel®1000 (CAS-Nr. 178463-23-5) by SOLABIA S. One or more humectants are optionally present at about 0.5 wt. % to about 8 wt. % in a topical cosmetic composition of the present invention, preferably about 1 wt. % to about 5 wt. %.

The aqueous phase of the preferred topical cosmetic compositions for use in the present invention can contain the usual cosmetic additives such as alcohols, especially lower alcohols, preferably ethanol and/or isopropanol, low diols or polyols and their ethers, preferably propyleneglycol, glycerin, ethyleneglycol, ethyleneglycol monoethyl- or monobutylether, propyleneglycol monomethyl- or -monoethyl- or-monobutylether, diethyleneglycol monomethyl- or monoethylether and analogue products, polymers, foam stabilizers; electrolytes and especially one or more thickeners. However, preferably the topical cosmetic compositions for use in the present invention are free of ethanol, more preferably they are free of alcohols, and most preferably they are free of organic solvents, since such compounds can cause skin irritation.

Thickeners that may be used in topical cosmetic compositions for use in the present invention to assist in making the consistency of a product suitable include carbomer, siliciumdioxide, magnesium and/or aluminium silicates, beeswax, stearic acid, stearyl alcohol polysaccharides and their derivatives such as xanthan gum, hydroxypropyl cellulose, polyacrylamides, acrylate crosspolymers preferably a carbomer, such as Carbopole® of type 980, 981, 1382, 2984, 5984 alone or mixtures thereof.

Suitable neutralizing agents which may be included in the topical cosmetic composition of the present invention to neutralize components such as e.g. an emulsifier or a foam builder/stabilizer include but are not limited to alkali hydroxides such as a sodium and potassium hydroxide; organic bases such as diethanolamine (DEA), triethanolamine (TEA), aminomethyl propanol, and mixtures thereof; amino acids such as arginine and lysine and any combination of any foregoing. The neutralizing agent can be present in an amount of about 0.01 wt. % to about 8 wt. % in the topical cosmetic composition of the present invention, preferably, 1 wt. % to about 5 wt. %.

The addition of electrolytes into the topical cosmetic composition for use according to the present invention may be necessary to change the behavior of a hydrophobic emulsifier. Thus, the emulsions/microemulsions for use according to this invention may contain preferably electrolytes of one or several salts including anions such as chloride, sulfates, carbonate, borate and aluminate, without being limited thereto. Other suitable electrolytes can be on the basis of organic anions such as, but not limited to, lactate, acetate, benzoate, propionate, tartrate and citrate. As cations preferably ammonium, alkylammonium, alkali- or alkaline earth metals, magnesium-, iron- or zinc-ions are selected. Especially preferred salts are potassium and sodium chloride, magnesium sulfate, zinc sulfate and mixtures thereof. Electrolytes can be present in an amount of about 0.01 wt. % to about 8 wt. % in the topical cosmetic composition of the present invention.

It is also an object of the present invention to provide a cosmetic composition comprising a *Gentiana acaulis* extract, *Gentiana septemfida* extract, or mixture thereof, and a conventional cosmetic carrier. Preferred cosmetic carrier for the present invention is glycerin.

The present invention also relates to the use of a cosmetic composition as described above for cosmetic application to the skin of a human being. The cosmetic application is preferably topical, and performed by application at least once per day, e.g. twice or triple times a day on the skin, preferably on the face.

The cosmetic application according to the present invention is selected from combating skin ageing and in particular appearance of wrinkles, including inhibiting inflammation of skin cells, retarding ageing, stimulating the synthesis of proteins by cells of the dermis and epidermis, protecting skin cells against oxidative stress, stimulating the synthesis of glycosaminoglycans by dermis cells, inhibiting collagenase and/or elastase in skin cells. More particularly, it is selected from induction of collagen IV synthesis, increase in hyaluronan production, decrease in caspasae-3, induction of pro-inflammatory cytokines.

Furthermore, the present invention relates to a method of cosmetic treatment said method comprising topically applying onto the skin of an individual seeking such treatment a cosmetic composition comprising a gentiopicroside free *Gentiana acaulis* extract, a gentiopicroside free *Gentiana septemfida* extract, or a mixture thereof as defined in all previous embodiments of the invention.

The term 'an effective amount' refers to an amount necessary to obtain a physiological effect. The physiological effect may be achieved by one application dose or by repeated applications. The dosage administered may, of course, vary depending upon known factors, such as the frequency of treatment; and the effect desired and can be adjusted by a person skilled in the art.

The present invention also relates to a method as described above, wherein, from about 0.2 μg to about 200 μg of a gentiopicroside free *Gentiana acaulis* extract, gentiopicroside free *Gentiana septemfida* extract, or a mixture thereof as defined in all previous embodiments of the invention, is applied per square centimeter of skin per day.

The usefulness of agents in combatting skin aging can be determined by methods known in the art.

The invention is further illustrated by the Examples which follow without being limited thereto.

EXAMPLES

Example 1: Skin Care Composition

| O/W-Emulsions | 2.1 Wt. % | 2.2 Wt. % |
|---|---|---|
| Cetearyl Alcohol + Sodium Cetylstearylsulfat | 3.00 | 2.00 |
| Glycerylstearat SE | 2.00 | 4.00 |
| Octyldodecanol | 2.00 | 2.00 |
| C12-15 Alkylbenzoate | 1.00 | 1.00 |
| C13-16 Isoparaffin | 3.00 | 3.00 |
| Caprylic acid-/Capric acid triglyceride | 2.00 | 2.00 |
| Glycerine | 5.00 | 6.00 |
| Dimethicone | 0.50 | 0.50 |
| Sodium ascorbylphosphate | 0.10 | — |
| Ethylhexylsalicylate | 0.50 | 0.50 |
| Glycyrrhetic acid | — | 0.10 |
| *Gentiana acaulis* extract | 1.00 | 1.50 |
| Grape seed oil | 0.50 | 0.50 |
| Dihydroxyacetone | — | 2.00 |
| Paraffinum Liquidum + Ginkgo Biloba Extract | 0.25 | 0.25 |
| Citric acid | 0.09 | 0.09 |
| Sodium citrate | 0.17 | 0.17 |
| Xanthan gum | — | 0.10 |
| Ammonium Acryloyldimethyltaurate/VP Copolymer | 0.40 | — |
| Carbomer | — | 0.30 |
| Parabene | 0.30 | 0.30 |
| Phenoxyethanol | 0.50 | 0.50 |
| Alcohol Denat. | 3.50 | 3.50 |
| Perfume | q.s | q.s |
| Water | ad 100 | ad 100 |

| Sprayable emulsions | 2.3 Wt. % | 2.4 Wt. % |
|---|---|---|
| Isoceteth-20 | 5.00 | 3.00 |
| Glycerylisostearate | 3.00 | 2.00 |
| Mineral Oil | 5.00 | 4.00 |
| Glycerine | 4.00 | 5.00 |
| Tocopherylacetate | 0.50 | 0.40 |
| *Gentiana acaulis* extract | 0.20 | 0.50 |
| Natriumcitrate | 0.40 | 0.40 |
| Phenoxyethanol | 0.40 | 0.40 |
| Citric acid | 0.20 | 0.20 |
| DMDM Hydantoin | 0.20 | 0.20 |
| Perfume | q.s. | q.s. |
| Water | ad 100 | ad 100 |

| O/W-Emulsions | 2.5 wt. % | 2.6 wt. % | 2.7 wt. % |
|---|---|---|---|
| Stearic acid | 2.00 | 3.00 | 3.00 |
| Glycerylstearat | 2.00 | 2.00 | 1.00 |
| Sorbitanstearat | — | 1.00 | — |
| Dicaprylyl Ether | 3.00 | 3.00 | — |
| Caprylic acid-/Capric acid triglyceride | 3.00 | 3.00 | — |
| Cetearyl Alcohol | 2.00 | 2.00 | — |
| Cetyl Alcohol | — | — | 1.00 |
| Stearyl Alcohol | — | — | 3.00 |
| Hydrogenated Coco-Glycerides | — | — | 4.00 |
| Mineral Oil | — | — | 3.00 |
| PEG-100 stearat | — | 1.00 | 0.50 |
| Trisodium EDTA | — | — | 1.00 |
| Glycerine | 4.00 | 6.00 | 10.00 |
| Dimethicone | — | — | 1.00 |
| Glycyrrhetic acid | 0.20 | — | — |
| *Gentiana acaulis*/*Gentiana septemfida* extract in a ratio 15/85 | 0.20 | 0.50 | 0.10 |
| Erythrulose | — | 4.00 | |
| Phenoxyethanol | 0.40 | 0.40 | 0.40 |
| Parabene | 0.20 | 0.20 | 0.20 |
| Citric acid | — | — | 0.09 |

| | | | |
|---|---|---|---|
| Carbomer | 0.20 | 0.20 | 0.20 |
| Perfume | q.s. | q.s. | q.s. |
| Water | ad 100 | ad 100 | ad 100 |

| O/W-Emulsions | 2.8 Wt. % | 2.9 wt. % |
|---|---|---|
| Glycerylstearate | 3.00 | 4.00 |
| C12-15 Alkylbenzoate | 4.00 | 4.00 |
| Caprylic acid-/Capric acid triglyceride | 3.00 | 2.50 |
| Isopropylstearat | 2.00 | 2.50 |
| Cetyl Alcohol | 2.00 | 2.00 |
| Stearyl Alcohol | 2.00 | 2.00 |
| Glycerin | 3.00 | 5.00 |
| Dimethicone | 0.50 | 2.00 |
| Glycyrrhetic acid | — | 0.10 |
| *Gentiana acaulis/Gentiana septemfida* extract in a ratio 15/85 | 1.00 | 0.50 |
| Phenoxyethanol | 0.40 | 0.40 |
| Parabene | 0.20 | 0.20 |
| Carbomer | 0.10 | 0.10 |
| Perfume | q.s. | q.s. |
| Water | ad 100 | ad 100 |

| Tanning Spray | 2.10 Wt. % |
|---|---|
| Butyl methoxydibenzoylmethane | 5.00 |
| Octocrylene | 10.00 |
| Homosalate | 5.00 |
| Glycerine | 0.50 |
| *Gentiana acaulis/Gentiana septemfida* extract in a ratio 15/85 | 0.50 |
| Perfume | q.s. |
| Ethanol | ad 100 |

| Emulsions-Fluid | 2.11 Wt. % |
|---|---|
| Stearic acid | 2.00 |
| Dicaprylylether | 3.00 |
| Octyldodecanol | 2.00 |
| C12-15 Alkylbenzoate | 4.00 |
| Cetylalcohol | 2.00 |
| Cetearyl Ethylhexanoate + Isopropyl myristate | 2.00 |
| Glycerine | 5.00 |
| Ethylhexylmethoxycinnamate | 2.00 |
| TiO2 | 1.00 |
| Cetylpalmitate | 1.00 |
| Glyceryl Stearate | 1.00 |
| Phenoxyethanol | 0.40 |
| Butyl Methoxydibenzoxylmethane | 2.00 |
| Perfume | q.s. |
| EDTA | 0.20 |
| Carbomer | 0.20 |
| Magnesium Aluminium Silicate | 0.20 |
| Paraben | 0.20 |
| Vitamin E Acetat | 0.10 |
| *Gentiana acaulis/Gentiana septemfida* extract in a ratio 15/85 | 0.10 |
| Paraben | 0.05 |
| BHT | 0.05 |
| DHA | 1.00 |

| O/W-Emulsion: night cream | 2.12 Wt. % |
|---|---|
| Glycerylstearatcitrate | 2.00 |
| Stearylalcohol | 2.00 |
| Cetylalcohol | 2.00 |
| Hydrogenated Coco Glyceride | 1.00 |
| Caprylic acid-/Capric acid triglyceride | 3.00 |
| Ethylhexylkcoco fatty acid esters | 2.00 |
| Dicaprylylether | 2.00 |
| C12-15 Alkylbenzoate | 3.00 |
| Tocopherylacetate | 1.00 |
| Ubichinon (Coenzyme Q10) | 0.10 |
| Sodium ascorbylphosphate | 0.10 |
| *Gentiana acaulis/Gentiana septemfida* extract in a ratio 15/85 | 1.00 |
| Parabene | 0.40 |
| Methylpropandiol | 1.00 |
| Carrageenan | 0.10 |
| Carbomer | 0.20 |
| Tapioca starch | 2.00 |
| EDTA | 0.20 |
| Glycerine | 5.00 |
| Waster and/or oil soluble dyes | 0.05 |
| Filling agents/Additives | 0.50 |
| Perfume | q.s. |
| Water | ad 100 |

The pH of the formulation is adjusted to about pH 6.5

| O/W-Emulsion: day cream | 2.13 Wt. % | 2.14 Wt. % |
|---|---|---|
| PEG-40-Stearat | 1.00 | 1.00 |
| Glycerylstearate | 3.00 | 3.00 |
| Cetearylalcohol | 2.00 | 2.00 |
| Dimethicone | 1.00 | 1.00 |
| Hydrogenated Coco Glycerides | 2.00 | 2.00 |
| Caprylic acid-/Capric acid triglyceride | 2.00 | 2.00 |
| Octyldodecanol e | 2.00 | 2.00 |
| Dicaprylylcarbonate | 2.00 | 2.00 |
| C12-15 Alkylbenzoate | 3.00 | 3.00 |
| Ethylhexyl methoxycinnamate | 4.00 | 4.00 |
| Butyl methoxydibenzoylmethane | 2.00 | 2.00 |
| Tocopherylacetate | 1.00 | 1.00 |
| Panthenol | 0.50 | 0.50 |
| Sodium ascorbylphosphate | 0.10 | 0.10 |
| Ammonium Acryloyldimethyltaurate/VP Copolymer | — | 0.40 |
| Glycyrrhetic acid | — | 0.10 |
| *Gentiana acaulis/Gentiana septemfida* extract in a ratio 15/85 | 1.00 | 0.50 |
| Nylon-12 | 3.00 | — |
| Distarch phosphate | — | 2.00 |
| Parabene | 0.40 | 0.40 |
| Methylpropandiol | 1.00 | 1.00 |
| Carbomer | 0.20 | 0.20 |
| Xanthan gum | 0.10 | 0.10 |
| EDTA | 0.20 | 0.20 |
| Glycerine | 8.00 | 8.00 |
| Tapioca starch | 0.05 | 0.05 |
| Filling agents/Additives | 0.30 | 0.30 |
| Perfume | q.s. | q.s. |
| Water | ad 100 | ad 100 |

| O/W-Emulsion: facial cream | 2.15 Wt. % | 2.16 Wt. % |
|---|---|---|
| Polyglyceryl-3-Methylglucosedistearate | 2.00 | 2.00 |
| Sorbitanstearate | 3.00 | 3.00 |
| Cetylalcohol | 2.00 | 2.00 |
| Myristylmyristate | 1.00 | 1.00 |
| Dicaprylylether | 3.00 | 3.00 |
| Octyldodecanol | 2.00 | 2.00 |
| C12-15 Alkylbenzoate | 3.00 | 3.00 |
| Cetearyl Ethylhexanoat + Isopropylmyristate | 2.00 | 2.00 |
| Ethylhexyl methoxycinnamate | 2.00 | 2.00 |
| Ethylhexyltriazone | 1.00 | 1.00 |
| Butyl Methoxydibenzoxylmethane | 2.00 | 2.00 |
| Magnesium Aluminium Silicate | 0.20 | 0.20 |
| Glycerine | 5.00 | 5.00 |
| Phenoxyethanole | 0.40 | 0.40 |
| Parabene | 0.30 | 0.30 |
| Vitamin E Acetate | 0.10 | 0.10 |
| Glycyrrhetic acid | — | 0.10 |
| *Gentiana acaulis/Gentiana septemfida* extract in a ratio 15/85 | 1.50 | 1.00 |
| BHT | 0.05 | 0.05 |
| EDTA | 0.20 | 0.20 |
| Carbomer | 2.00 | 0.20 |
| Perfume | q.s. | q.s. |
| Water | ad 100 | ad 100 |

Example 2: Preparation of a Gentiopicroside/Gentiopicral Free *Gentiana* Extract a—Preparation of the Enzyme Bound on Solid Phase (Step Known from the Literature)

The enzyme β-glucosidase (EC 3.2.1.21) (100 mg) was incubated with 15.4 mg of glucose dissolved in 82 ml of buffer solution (pH=7.75) at room temperature for 1 hour.

The resin Purolite ECR 8214F is mixed separately with 30 ml of buffer solution (pH=7.75) for 5 minutes and then filtered (washing step).

The filtered resin was then added to the buffer solution containing the enzyme at 25° C. and mixed gently for 24 hours. After 24 hours, the solution was filtered and the resulting resin was washed with 60 ml of buffer solution (pH=7.75) and twice 60 ml of deionized water. The resin was then mixed in 80 ml of buffer solution (pH=7.75) and 1 ml of BSA (Bis(trimethylsilyl)acetamide) was added. The suspension was mixed gently for 24 hours. After 24 hours, the resin was filtered and washed twice with 100 ml deionized water.

The buffer solution is a mixture of 14.4 ml of solution $KH_2PO_4$ (68 g/500 ml) and 86.6 ml of solution $K_2HPO_4$ (87.1 g/500 ml).

b—Preparation of the Gentiopicroside Free *Gentiana* Extract: Transformation of the Gentiopicroside into the Gentiopicral in *Gentiana* Extract.

b-1) An extract of 50 g of the aerial parts (flower, leaf, stem) of rare alpine plants from the *Gentian* species (*Gentiana acaulis* and/or *Gentiana septemfida*) was prepared as followed: chopped dried plants were extracted twice with 10 times (w/w) of 60% ethanol (with active carbon) for 2 hours at 50° C. The extract was then filtered and concentrated in a Rotavapor device at 50° C. and 50 mbar atmosphere to obtain a concentrated aqueous solution. Pure ethanol (5 times the quantity in weight of the aqueous solution) was added into this concentrate in order to precipitate sugars and proteins, then, after filtration, ethanol was removed once again in a Rotavapor device resulting in about 54 g of an aqueous extract comprising about 36% (area %) of gentiopicroside (determined by UPLC: C18 reversed phase column, eluen:water/acetonitrile, detection: 254 nm) which was used in in the subsequent step b-2):

b-2) The aqueous solution obtained as described in b-1) was placed in a flask at 28° C. (bath) and the enzyme (5 g) prepared in step a) (white powder) was added to extract solution. The reaction was done during a few days and was followed by UPLC. The percentage of transformation of the gentiopicroside was closely monitored. If necessary, a supplementary amount of bound enzyme was adde. When the gentiopicroside was completely transformed into gentiopicral, the reaction was terminated by filtration and subsequent washing of the filtered resin with 50 ml of deionized water. The washing solution was collected together with the main solution.

The solid phase bound with the enzyme was washed and dried (lyophilized) in order to be re-used.

c—Removal of the Gentiopicral.

The obtained solution in step b-2) (100 ml) was extracted twice with an equal amount of ethyl acetate (100 ml). The organic and aqueous phase were then separated. The aqueous solution was analyzed by UPLC: C18 reversed phase column, eluent: water/acetonitrile, detection: 254 nm.) to determine if gentiopicral was completely removed. If necessary a third extraction with 100 ml ethyl acetate was performed. The obtained aqueous phase was distilled under vacuum in order to remove remaining traces of ethyl acetate.

The aqueous solution finally obtained can be used for formulation directly or for dry extract manufacturing.

The studies were performed with the extracts from individual Gentian or as mixtures of both plants in a ratio of *Gentiana acaulis/Gentiana septemfida*, 15/85 mass/mass or 25/75 mass/mass.

Example 3: Effect of a *Gentiana* Extract on Hyaluronan Production

*Gentiana* extract (*Gentiana acaulis/Gentiana septemfida*, 25/75 m/m) was used. Normal human fibroblasts (NHF) P2+1 were seeded at 5000 cell/well in 96 well cell culture plates (Nunclon) in MEM 10% FCS (Pan Biotech). After three days of growth, *Gentiana* extract solution was added in medium without FCS and incubated the cells for an additional three days. Secreted hyaluronan in the growth medium was measured using a Hyaluronan Assay Kit (K-1200, Echelon, Salt Lake City, Utah).

Compared to untreated cells we showed a 26±4.9% increase in hyaluronan production with 0.001% *Gentiana* extract and TGFbeta1 (10 ng/ml), served as positive control, stimulated by 45.6±1.1%.

Example 4: Effect of a *Gentiana* Extract on CPD Repair (Cyclobutane Pyrimidine Dimer)

An average of 400000 cells were seeded into 6 well plates. After over-night incubation in growth medium cells were washed twice with PBS, overlaid with 1 ml PBS, and irradiated with 20 mJ/cm2 UVB. Afterwards, the cells were incubated with growth medium and *Gentiana* extract. At defined time-points cells were trypsinized, and DNA was isolated using a DNA-Isolation Kit from Qiagen. 200 ng of DNA was spotted onto ELISA-plates and CPDs were detected using a biotinylated anti-CPD-antibody from Kamiya at 1:2000 dilution. The extract consists of *Gentiana acaulis* & *Gentiana septemfida*, 25/75 m/m.

These results in table below show a 40% increase of CPD repair after 4 hours with 0.1% Gentian extract.

| Hours after UVB (20 mJ/cm2) | Relative CPD staining of control (Untreated) | Relative CPD staining of treated with 0.1% Gentian extract |
|---|---|---|
| 0 | 100% | 100% |
| 2 | 95.4% | 101.1% |
| 4 | 75.0% | 33.9% |
| 24 | 29.2% | 6.7% |

Example 5: Effect of a *Gentiana* Extract on Pro-Inflammatory Cytokines & MMPs Material & Method
Measurement of Cytokines and MMPs Normal human keratinocytes (NHK) P4+1 were grown to sub-confluency in CnT-07 growth medium (CELLnTEC, Berne, Switzerland). After irradiation with 100 mJ/cm$^2$ UVB with a solar light simulator (SOL500RF, Dr. Hoenle, Germany), cells were incubated again for 24 hrs in CnT-07 containing 0.1% *Gentiana* extract (*Gentiana acaulis* & *Gentiana septemfida*, 25/75 m/m) or vehicle. Cell culture supernatant was collected over time and frozen at −20 C until cytokines and MMPs were measured in a Luminex100 device. Luminex100 measurements were performed using a multiplex custom made kit (Panomics, Italy) according to manufacturer's instructions.

An inhibition of pro-inflammatory cytokines IL-1β, IL-8, TNFα, MMP-1 release was found as highlighted in the table below Table with results for example 8: %-Inhibition of cytokine release of UVB-irradiated cells treated with 0.1% *Gentiana* extract compared to UV irradiated—but untreated cells.

|      | IL-1beta | TNFalpha | IL-8  | MMP-1 |
|------|----------|----------|-------|-------|
| 2 h  | 78%      | 0%       | 80%   | 83%   |
| 4 h  | 87%      | 31.2%    | 74.3% | 82.3% |
| 8 h  | 80.7%    | 95.7%    | 80%   | 94%   |
| 24 h | 37%      | 77.9%    | 31%   | 56.9% |

Example 6: Reduction of Intracellular Reactive Oxygen Species Production by a *Gentiana* Extract Detection of Reactive Oxygen Species (ROS)

Intracellular ROS generation was determined using ROS specific probe $H_2$DCF-DA (Molecular Probes). Oxidation of $H_2$DCF-DA to the fluorescent product DCF serves an indicator of the overall degree of intracellular oxidative stress.

Primary human fibroblasts were seeded at 5000 cells/well in 96 well cell culture plates in DMEM, 10% FCS, 1% Pen/Strep. After 24 h *Gentiana* extract (*Gentiana acaulis* & *Gentiana septemfida*, 25/75 m/m) was added solution and incubated the cells for additional 72 h. After compound treatment we incubated the cells with $H_2$DCF-DA (25 µM) and Hoechst 33258 (1 ug/ml) in HBSS/2.5% HEPES for 45 min at 37° C. in the dark. We washed the cells twice with HBSS/HEPES to remove any $H_2$DCF-DA which has not been internalised and subjected them to 30% $H_2O_2$. ROS production was measured in a fluorescent plate reader (SpectraMax GeminiXS) after 30 min (at 520 nM), and normalized to the DNA content.

In this study we showed compared to untreated cells a 30% reduction of intracellular ROS production in cells treated with 0.05% *Gentiana* extract.

All this data demonstrate a positive effect on photo-aging and anti-aging in vitro.

The invention claimed is:

1. A method for combatting skin aging by reducing wrinkles, inducing collagen synthesis, and/or reducing intracellular reactive oxygen species production in skin of a patient in need thereof, wherein the method comprises topically applying to the skin of the patient an effective amount of a cosmetic composition comprised of a substantially gentiopicroside-free extract of *Gentiana acaulis* and/or *Gentiana septemfida*, and observing the skin aging combatting effects thereof, wherein the substantially gentiopicroside-free extract comprises gentiopicral hydrolyzed from gentiopicroside.

2. The method according to claim 1, wherein the cosmetic composition comprises between 0.001 and 20 wt. % in dry matter, based on the total weight of the cosmetic composition, of the substantially gentiopicroside-free extract of *Gentiana acaulis* and/or *Gentiana septemfida*.

3. The method according to claim 1, wherein the cosmetic composition further comprises glycerin.

4. The method according to claim 1, wherein the gentiopicral is present in the cosmetic composition in an amount of less than 1%.

5. The method according to claim 1, wherein the cosmetic composition comprises less than 0.1% concentration of gentiopicroside.

6. The method according to claim 1, wherein the cosmetic composition comprises no detectable gentiopicroside.

7. A method for combatting skin aging by reducing wrinkles, inducing collagen synthesis, and/or reducing intracellular reactive oxygen species production in skin of a patient in need thereof, wherein the method comprises topically applying to the skin of the patient an effective amount of a cosmetic composition comprised of a substantially gentiopicroside-free extract of *Gentiana acaulis* and/or *Gentiana septemfida* in a mass ratio of *Gentiana acaulis* to *Gentiana septemfida* between 5/95 and 50/50, and observing the skin aging combatting effects thereof.

8. The method according to claim 7, wherein the mass ratio of *Gentiana acaulis* to *Gentiana septemfida* is between 10/90 and 30/70.

9. The method according to claim 7, wherein the mass ratio of *Gentiana acaulis* to *Gentiana septemfida* is between 15/85 and 25/75.

* * * * *